United States Patent
Xu et al.

(10) Patent No.: US 11,505,530 B2
(45) Date of Patent: Nov. 22, 2022

(54) 1,8-NAPHTHALIMIDE DERIVATIVE, PREPARATION METHOD THEREFOR AND USE THEREOF

(71) Applicant: SOOCHOW UNIVERSITY, Suzhou (CN)

(72) Inventors: Dongmei Xu, Suzhou (CN); Yufen Chen, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 335 days.

(21) Appl. No.: 16/766,798

(22) PCT Filed: Apr. 10, 2018

(86) PCT No.: PCT/CN2018/082584
§ 371 (c)(1),
(2) Date: May 26, 2020

(87) PCT Pub. No.: WO2019/196022
PCT Pub. Date: Oct. 17, 2019

(65) Prior Publication Data
US 2020/0385356 A1 Dec. 10, 2020

(51) Int. Cl.
*C07D 211/00* (2006.01)
*C07D 221/14* (2006.01)
(Continued)

(52) U.S. Cl.
CPC ............ *C07D 221/14* (2013.01); *G01J 3/465* (2013.01); *G01N 21/64* (2013.01); *G01N 21/80* (2013.01)

(58) Field of Classification Search
CPC .................................................... C07D 221/14
(Continued)

(56) References Cited

FOREIGN PATENT DOCUMENTS

| CN | 102533255 A | 7/2012 |
|----|-------------|--------|
| CN | 103664971 A | 3/2014 |

(Continued)

OTHER PUBLICATIONS

Wang et al. "A Naphthalimide-Based Glyoxal Hydrazone for Selective Fluorescence Turn-On Sensing of Cys and Hcy" Org. Lett., vol. 14, No. 2, 2012 (Year: 2012).*

(Continued)

*Primary Examiner* — Christine T Mui
*Assistant Examiner* — Emily R. Berkeley
(74) *Attorney, Agent, or Firm* — SZDC Law P.C.

(57) ABSTRACT

Disclosed are a 1,8-naphthalimide derivative, a preparation method therefor and a use thereof. The 1,8-naphthalimide derivative is easy to prepare, and is an enhanced $Cu^{2+}$ fluorescent probe, which can detect $Cu^{2+}$ by two wavelengths and be applied to almost-all-water systems. According to atitration experiments and blank experiments at 392 nm and 754 nm, the detection limit of the 1,8-naphthalimide derivative of the present invention for $Cu^{2+}$ is $2.6368 \times 10^{-7}$ mol/L and $2.0156 \times 10^{-7}$ mol/L, respectively, indicating that same can perform quantitative detection for $Cu^{2+}$ with a high selectivity and a high sensitivity by using two wavelengths. In addition, a pH colorimetric switch based on 1,8-naphthalimide can rapidly and reversibly respond to a pH by means of three ways: a maximum absorption wavelength, absorbance and color change. Same has a narrow switching pH range, a good selectivity and a high sensitivity, can be used in almost-all-water systems.

12 Claims, 13 Drawing Sheets

(51) Int. Cl.
*G01J 3/46* (2006.01)
*G01N 21/64* (2006.01)
*G01N 21/80* (2006.01)

(58) Field of Classification Search
USPC .......................................................... 436/172
See application file for complete search history.

(56) References Cited

FOREIGN PATENT DOCUMENTS

| CN | 106478602 A | 3/2017 |
|---|---|---|
| CN | 106518870 A | 3/2017 |
| CN | 107501179 A | 12/2017 |
| CN | 108387544 A | 8/2018 |
| CN | 108395403 A | 8/2018 |

OTHER PUBLICATIONS

Chen, Jiayi et al. "1,8-Naphthalimide-based turn-on fuorescent chemosensor for Cu2+ and its application in bioimaging", Journal of Luminescence, No. 180, Aug. 24, 2016, pp. 301-305.
Chen, Zhijun et al., "Highly selective fluorescence turn-on chemosensor based on naphthalimide derivatives for detection of copper(II) ions", Spectrochimica Acta Part A: Molecular and Biomolecular Spectroscopy, No. 105, Dec. 14, 2012, pp. 57-61.

* cited by examiner

1,8-NAPHTHALIMIDE DERIVATIVE, PREPARATION METHOD THEREFOR AND USE THEREOF

This application is the National Stage Application of PCT/CN2018/082584, filed on Apr. 10, 2018, which is incorporated by reference for all purposes as if fully set forth herein.

FIELD OF THE INVENTION

The present invention belongs to the technical field of fluorescent probes, and specifically relates to a 1,8-naphthalimide derivative, a preparation method therefor and a use thereof.

BACKGROUND OF THE INVENTION 1,8-naphthalimide compounds under light will undergo intramolecular charge transfer between a substituent at the 4-position C of a naphthalene ring and an iminocarbonyl, which will result in changes in fluorescence emission wavelength and fluorescence intensity; besides, they have strong photostability, high fluorescence quantum yield, large Stokes shift, and easy molecular structure modification. Therefore, they are widely used in fiber dyeing, fluorescence recognition and labeling, photoelectric materials and other different fields. For the 1,8-naphthalimide compounds, different modifications will bring different effects and applications. For example, structure 1 is a fluorescent dye for fibers, structure 2 is a $Hg^{2+}$ fluorescent probe, and structure 3 is used as a photoelectric material.

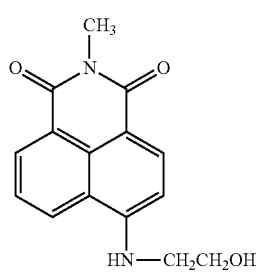

structure 1

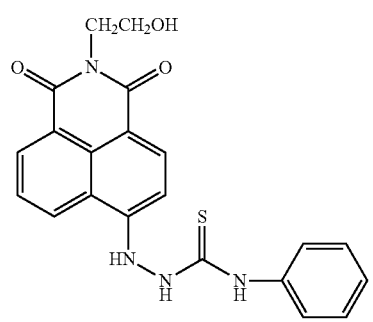

structure 2

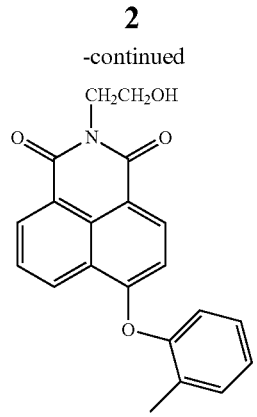

structure 3

$Cu^{2+}$, as a trace element, plays an important role in human life activities. The deficiency of $Cu^{2+}$ will cause various problems of blood, nervous system, etc.; however, excessive $Cu^{2+}$ can also be potentially toxic to human living cells, and lead to cardiovascular and neurodegenerative diseases including Wilson's disease, Alzheimer's disease, prion diseases, and so on. In recent years, the content of $Cu^{2+}$ in many water bodies has exceeded the standard seriously due to excessive discharge of factories and other reasons. According to the Environmental Protection Agency (EPA), the maximum concentration of $Cu^{2+}$ in drinking water must not exceed 20 µM (R. Shen, J. J. Yang, H. Luo, B. Wang, Y. Jiang. A sensitive fluorescent probe for cysteine and $Cu^{2+}$ based on 1,8-naphthalimide derivatives and its application in living cells imaging. Tetrahedron 73 (2017) 373-377). Therefore, it is very important to detect $Cu^{2+}$ in biological and environmental systems. Using fluorescent probes to detect heavy metal ions has the advantages of simple method, low cost, high sensitivity, good selectivity, and quick response. Some fluorescent probes have been used to detect $Cu^{2+}$. In summary, most of the $Cu^{2+}$ fluorescent probes based on 1,8-naphthalimide are of a quenching type and have low sensitivity; moreover, some of them have complex structure and are difficult to synthesize, some of them have weak anti-interference ability, and some of them can only be used in an organic solvent system and have poor practicability.

As an important parameter in many chemical and biological processes, pH plays a vital role in chemical reactions, natural environment, biological cells and tissue activities (J. Chao, H. Wang, Y. Zhang, C. Yin, F. Huo, K. Song, Z. Li, T. Zhang, Y. Zhao. A novel 'donor-π-acceptor' type fluorescence probe for sensing pH: mechanism and application in vivo. Talanta 174 (2017) 468-476). For example, pH can be used to regulate chemical reactions, strong acids and bases may cause corrosion and burns, and abnormal pH may cause cardiopulmonary and neurological diseases. Therefore, monitoring pH is of great significance. The ultraviolet-visible (UV-Vis) absorption spectrum is favored by people because of its advantages such as fast response, high sensitivity, and visual recognition of signal response. The indication of signal change by the pH colorimetric switch that uses UV-Vis absorption spectrum to respond to pH mutation is usually discernible to the naked eye. It can display the pH change in the organism or environment in the most direct way, and is thus very meaningful to get studied. However, some existing pH colorimetric switches can only be used in strong acid or alkali systems, some have low sensitivity, some have a wide pH range for switching, and some have weak anti-interference ability. The pH colorimetric switch with excellent comprehensive performance needs to be developed urgently.

CONTENTS OF THE INVENTION

The enhanced $Cu^{2+}$ fluorescent probe based on 1,8-naphthalimide disclosed in the present invention has the advantages of high selectivity, high sensitivity, strong anti-interference ability, relatively easy synthesis, and application in almost-all-water systems. Besides, the present invention discloses a pH colorimetric switch based on 1,8-naphthalimide, which is relatively easy to synthesize, can respond to a pH by means of three ways, has a narrow switching pH range, responds rapidly and reversibly, and can be used in almost-all-water systems.

The present invention adopts the following technical solution:

A preparation method for a 1,8-naphthalimide derivative is provided, comprising the following steps:

(1) preparing an intermediate A using 4-bromo-1,8-naphthalic anhydride and n-butylamine as raw materials;

(2) preparing an intermediate B using the intermediate A and hydrazine hydrate as raw materials;

(3) preparing an intermediate C using the intermediate B and glyoxal as raw materials; and (4) preparing the 1,8-naphthalimide derivative using the intermediate C and trihydroxymethyl aminomethane as raw materials.

A $Cu^{2+}$ fluorescent probe system and a preparation method therefor, the method comprising the following steps:

(1) preparing an intermediate A using 4-bromo-1,8-naphthalic anhydride and n-butylamine as raw materials;

(2) preparing an intermediate B using the intermediate A and hydrazine hydrate as raw materials;

(3) preparing an intermediate C using the intermediate B and glyoxal as raw materials;

(4) preparing the 1,8-naphthalimide derivative using the intermediate C and trihydroxymethyl aminomethane as raw materials; and (5) adding the 1,8-naphthalimide derivative to a solvent to prepare the $Cu^{2+}$ fluorescent probe system, the solvent being an organic solvent and/or water.

In step (5) of the above technical solution, the organic solvent is acetonitrile; when the solvent is an organic solvent and water, the volume ratio of the organic solvent to water is less than or equal to 1/99.

A method for detecting the content of $Cu^{2+}$ in the system is provided, comprising the following steps:

(1) preparing an intermediate A using 4-bromo-1,8-naphthalic anhydride and n-butylamine as raw materials;

(2) preparing an intermediate B using the intermediate A and hydrazine hydrate as raw materials;

(3) preparing an intermediate C using the intermediate B and glyoxal as raw materials;

(4) preparing the 1,8-naphthalimide derivative using the intermediate C and trihydroxymethyl aminomethane as raw materials; and (5) adding the 1,8-naphthalimide derivative solution to the system, measuring fluorescence intensity, and then determining the content of $Cu^{2+}$ in the system according to a curve of relationship between the fluorescence intensity and the concentration of $Cu^{2+}$ in the system.

In the above technical solution, the final concentration of the 1,8-naphthalimide derivative is 10 µM.

When the 1,8-naphthalimide derivative of the present invention is used as a $Cu^{2+}$ fluorescent probe, the detection environment may be an organic solvent environment and/or a water environment; that is, the 1,8-naphthalimide derivative can be used to detect copper ions in water or a mixture of water and an organic solvent.

In step (1) of the present invention, the molar ratio of 4-bromo-1,8-naphthalic anhydride to n-butylamine is 1:1.3, and the intermediate A is prepared using 4-bromo-1,8-naphthalic anhydride and n-butylamine as raw materials in the presence of the organic solvent and under the protection of nitrogen. For example, under the protection of $N_2$, stirring 4-bromo-1,8-naphthalic anhydride and n-butylamine with acetic acid as the solvent to react at 120° C. for 6 h, then stopping the reaction, pouring the reaction solution into ice water to precipitate a light yellow solid, filtering, recrystallizing the filter cake with ethanol, and drying in vacuum to obtain a light yellow solid intermediate A.

In step (2) of the present invention, the molar ratio of the intermediate A to hydrazine hydrate is 1:5.3, and the intermediate B is prepared using the intermediate A and hydrazine hydrate as raw materials in the presence of the organic solvent. For example, refluxing the intermediate A and hydrazine hydrate with glycol monomethyl ether as the solvent to react at 125° C. for 5 h, then cooling to room temperature, pouring into 50 mL of water and stand still to form an orange-red precipitate, filtering, washing the filter cake twice with deionized water, and washing again with a small amount of ethanol, and then drying in vacuum to obtain an orange-red solid powder intermediate B.

In step (3) of the present invention, the molar ratio of the intermediate B to glyoxal is 1:(13.3 to 15.5), and the intermediate C is prepared using the intermediate B and glyoxal as raw materials in the presence of organic solvent. For example, stirring the intermediate B and glyoxal with anhydrous ethanol as the solvent to react at room temperature for 6 h, then stopping reaction, precipitate an orange solid, filtering, washing the filter cake once with ethanol and then twice with deionized water, and then drying in vacuum to obtain an orange intermediate C.

In step (4) of the present invention, the molar ratio of the intermediate C to trihydroxymethyl aminomethane is 1:(1 to 1.6), and the 1,8-naphthalimide derivative is prepared using the intermediate C and trihydroxymethyl aminomethane as raw materials in the presence of organic solvent. For example, making the intermediate C and trihydroxymethyl aminomethane react with one of anhydrous ethanol, anhydrous methanol and dichloromethane as the solvent at 25° C. to 80° C. for 6 h to 24 h, then removing the solvent by rotary evaporation, dispersing the residue in 10 mL of dichloromethane, filtering with suction to obtain an orange-red solid crude product, and then washing the crude product three times alternately and respectively with dichloromethane and deionized water to obtain an orange-red solid 1,8-naphthalimide derivative.

In the present invention, obtaining the curve of relationship between the fluorescence intensity and the concentration of $Cu^{2+}$ is a conventional technique. Standard solutions with different concentrations of $Cu^{2+}$ are prepared, and the fluorescence intensity of each standard solution is measured with the 1,8-naphthalimide derivative, respectively, and then a standard curve of $Cu^{2+}$ concentration-fluorescence intensity is obtained according to the relationship between the concentration and the fluorescence intensity.

The 1,8-naphthalimide derivative prepared in the present invention has the following chemical structural formula:

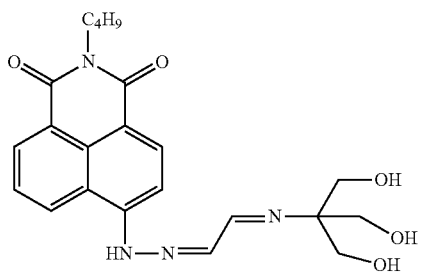

The 1,8-naphthalimide derivative of the present invention can have high selectivity and sensitivity to $Cu^{2+}$ by means of two wavelengths. Therefore, the present invention also discloses the use of the above 1,8-naphthalimide derivative as a $Cu^{2+}$ fluorescent probe, or the use of the $Cu^{2+}$ fluorescent probe system in detecting $Cu^{2+}$, with the application environment being an organic solvent and/or water environment.

The present invention also discloses the use of the above 1,8-naphthalimide as a pH colorimetric switch.

The present invention also discloses the use of the above 1,8-naphthalimide in the preparation of pH colorimetric switch materials.

The present invention also discloses a 1,8-naphthalimide-based pH colorimetric switch system comprising the above 1,8-naphthalimide and a solvent, the solvent being an organic solvent and/or water.

The present invention also discloses the use of the above 1,8-naphthalimide-based pH colorimetric switch system in pH colorimetry.

The present invention also discloses the use of the above 1,8-naphthalimide-based pH colorimetric switch system in the preparation of pH colorimetric switch materials.

A method for pH colorimetry of a solution to be tested is provided, comprising the following steps: Adding the above 1,8-naphthalimide solution to the solution to be tested to obtain a mixed system, then testing the UV-Vis (ultraviolet-visible) absorption spectrum of the mixed system, and completing the pH colorimetry of the solution to be tested according to color of the mixed system, UV-Vis absorption wavelength, and absorbance. The concentration of 1,8-naphthalimide in the mixed system of the above technical solution is 10 µM; when the mixed system contains an organic solvent and water, the volume ratio of the organic solvent to water is less than 4. In the present invention, the environment for the use of 1,8-naphthalimide in pH colorimetry is an organic solvent and/or water environment. That is, when the 1,8-naphthalimide of the present invention is used as a pH colorimetric switch, the application environment may be an organic solvent, water, or a mixed environment of an organic solvent and water; and in the mixed environment of an organic solvent and water, the volume ratio of the organic solvent to water is less than 4, or even down to 1/99.

The preparation method of the present invention can be expressed as follows:

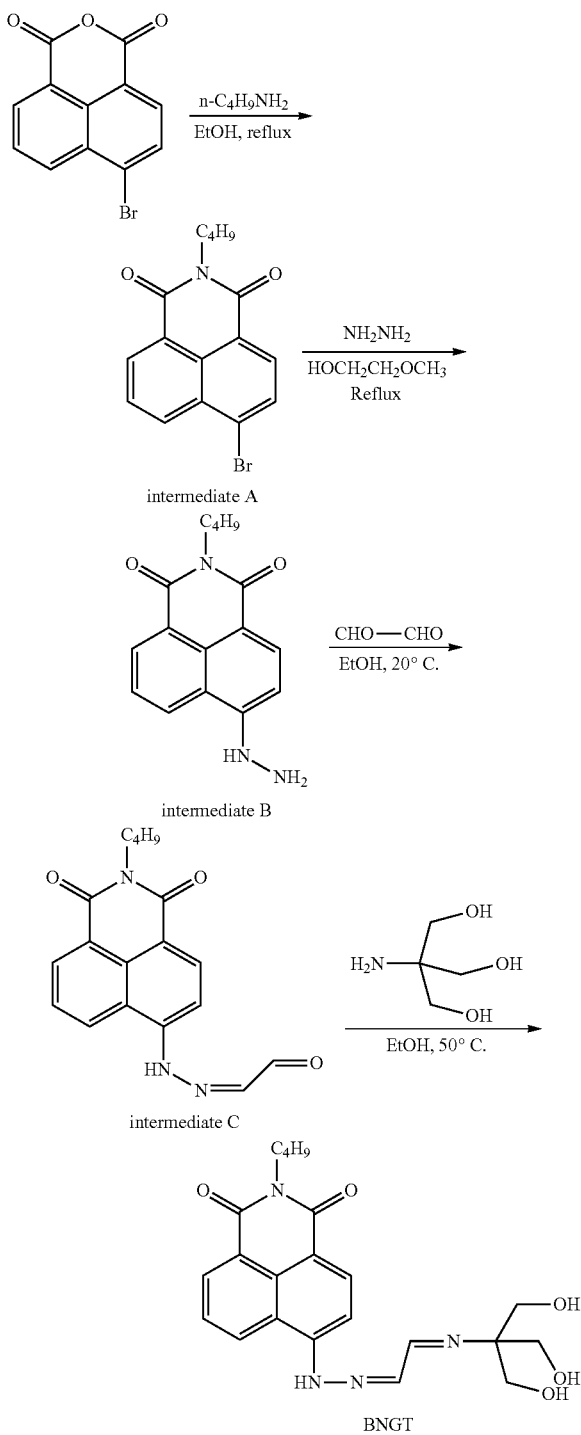

The present invention designs and synthesizes a novel 1,8-naphthalimide derivative BNGT, which is relatively easy to prepare, and is an enhanced $Cu^{2+}$ fluorescent probe that can detect $Cu^{2+}$ by means of two wavelengths, and can be especially applied to almost-all-water systems. According to atitration experiments and blank experiments at 392 nm and 754 nm, the detection limit of BNGT for $Cu^{2+}$ is $2.6368\times10^{-7}$ mol/L and $2.0156\times10^{-7}$ mol/L, respectively, indicating that BNGT can perform quantitative detection for $Cu^{2+}$ with a high selectivity and a high sensitivity by using two wavelengths. The 1,8-naphthalimide of the present invention can rapidly and reversibly respond to a pH by means of three ways: a maximum absorption wavelength, absorbance and color change. Same has a narrow switching pH range (from a pH of 5.8 to a pH of 6.0, only 0.2 pH units), a good selectivity and a high sensitivity, can be used in almost-all-water systems, and has a bright application prospective.

DETAILED DESCRIPTION OF THE EMBODIMENTS

Example 1: Preparation of Intermediate A

Figure 1:
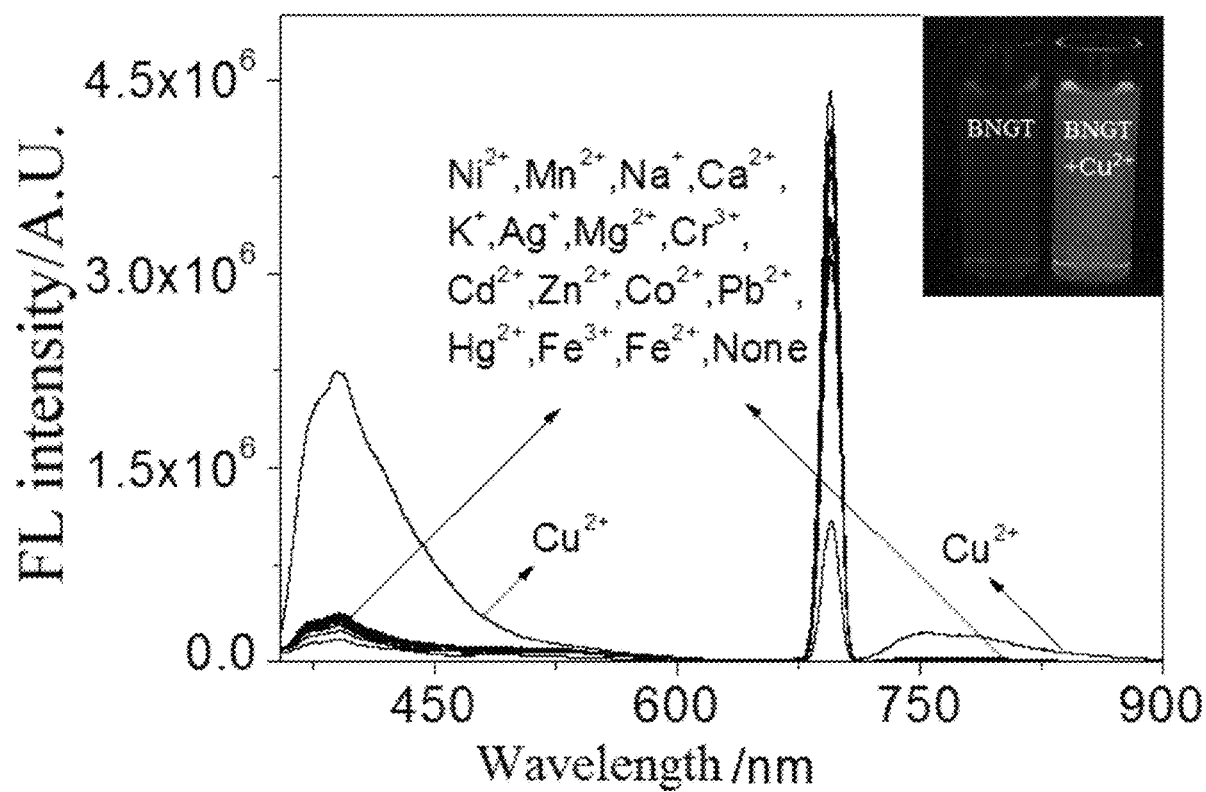
FIG. 1 shows the response of the fluorescence spectrum of BNGT to different metal ions.

Adding 4-bromo-1,8-naphthalic anhydride and n-butylamine in a molar ratio of 1:1.3 to acetic acid, and stirring them to react at 120° C. for 6 h under the protection of $N_2$, then stopping the reaction, pouring the reaction solution into ice water to precipitate a light yellow solid, filtering, recrystallizing the filter cake with ethanol, and drying in vacuum to obtain a light yellow solid intermediate A at a yield of 85.0%.

Example 2: Preparation of Intermediate B

Adding the intermediate A and hydrazine hydrate in a molar ratio of 1:5.3 to glycol monomethyl ether, and refluxing them to react at 125° C. for 5 h, then cooling to room temperature, pouring into 50 mL of water and stand still to form an orange-red precipitate, filtering, washing the filter cake twice with deionized water, and washing again with a small amount of ethanol, and then drying in vacuum to obtain an orange-red solid powder intermediate B at a yield of 87.7%.

Example 3: Preparation of Intermediate C

Adding the intermediate B and glyoxal in a molar ratio of 1:13.3 to anhydrous ethanol and stirring at room temperature for 6 h, then stopping the reaction to precipitate an orange solid, filtering, washing the filter cake once with ethanol and then twice with deionized water, and then drying in vacuum to obtain an orange intermediate C at a yield of 66.0%.

Adding the intermediate B and glyoxal in a molar ratio of 1:14 to anhydrous ethanol and stirring at room temperature for 6 h, then stopping the reaction to precipitate an orange solid, filtering, washing the filter cake once with ethanol and then twice with deionized water, and then drying in vacuum to obtain an orange intermediate C at a yield of 70.0%.

Adding the intermediate B and glyoxal in a molar ratio of 1:15.5 to anhydrous ethanol and stirring at room temperature for 6 h, then stopping the reaction to precipitate an orange solid, filtering, washing the filter cake once with ethanol and then twice with deionized water, and then drying in vacuum to obtain an orange intermediate C at a yield of 71.0%.

Example 4: Preparation of 1,8-Naphthalimide Derivative

Making the intermediate C (referred to as BNG) and trihydroxymethyl aminomethane in a molar ratio of 1:1.6 react at 50° C. for 7 h with anhydrous ethanol as the solvent under the protection of $N_2$, then cooling to room temperature, removing the solvent by rotary evaporation, dispersing the residue in 10 mL of dichloromethane, filtering with suction to obtain an orange-red solid crude product, and then washing the crude product three times alternately and respectively with dichloromethane and deionized water to obtain an orange-red powder target product 1,8-naphthalimide derivative called BNGT at a yield of 75.0%. Other synthesis conditions and corresponding yields of BNGT are shown in Table 1.

TABLE 1

| | Other synthesis conditions and corresponding yields of BNGT | | | | | |
|---|---|---|---|---|---|---|
| No. | Molar ratio of BNG to trihydroxymethyl aminomethane | Solvent | Reaction temperature (° C.) | Reaction time (h) | Under the protection of $N_2$ | Yield (%) |
| 1 | 1:1.0 | Anhydrous ethanol | 80 | 6 | Yes | 50.8 |
| 2 | 1:1.4 | Anhydrous ethanol | 80 | 6 | Yes | 54.2 |
| 3 | 1:1.6 | Anhydrous ethanol | 80 | 6 | Yes | 60.0 |

TABLE 1-continued

Other synthesis conditions and corresponding yields of BNGT

| No. | Molar ratio of BNG to trihydroxymethyl aminomethane | Solvent | Reaction temperature (° C.) | Reaction time (h) | Under the protection of $N_2$ | Yield (%) |
|---|---|---|---|---|---|---|
| 4 | 1:1.6 | Anhydrous ethanol | 60 | 6 | Yes | 71.4 |
| 5 | 1:1.6 | Anhydrous ethanol | 50 | 6 | Yes | 73.5 |
| 6 | 1:1.6 | Anhydrous ethanol | 25 | 6 | Yes | 30.5 |
| 7 | 1:1.6 | Anhydrous ethanol | 50 | 7 | Yes | 75.0 |
| 8 | 1:1.6 | Anhydrous ethanol | 50 | 10 | Yes | 73.2 |
| 9 | 1:1.6 | Anhydrous ethanol | 50 | 24 | Yes | 72.1 |
| 10 | 1:1.6 | Dichloromethane | 50 | 7 | Yes | 15.5 |
| 11 | 1:1.6 | Anhydrous ethanol | 50 | 7 | Yes | 45.0 |

Characterization of BNGT:

IR (KBr) cm$^{-1}$: 3441.56 (—OH), 2871.48, 2930.70, 2959.43 (CH$_3$, CH$_2$), 1687.05 (C=N), 1639.67 (C=O), 1388.96, 1426.57, 1585.09 (ArH), 1116.97 (C—N). $^1$H NMR (DMSO-d$_6$, 400 MHz): δ ppm 0.91-0.95 (t, 3H, CH$_3$), 1.34-1.36 (m, 2H, CH$_2$), 1.59-1.60 (m, 2H, CH$_2$), 3.60-3.62 (m, 2H, CH$_2$), 4.00 (s, 2H, CH$_2$), 4.50-5.08 (m, 3H, OH), 7.51-7.53 (d, 1H, J=8.4, ArH), 7.77-7.79 (m, 1H, CH), 7.82-7.87 (m, 1H, ArH), 8.40-8.42 (d, 1H, J=8.4, CH), 8.48-8.50 (m, 1H, ArH), 8.68-8.73 (t, 1H, J=8.4 Hz, ArH), 9.62-9.64 (d, 1H, J=8, ArH), 12.21 (s, 1H, NH). $^{13}$C NMR (DMSO-d$_6$, 400 MHz) δ: 163.95, 163.07, 146.83, 140.34, 133.15, 131.69, 128.28, 126.30, 122.60, 120.04, 114.87, 111.46, 109.46, 67.47, 61.58, 39.04, 29.85, 19.90, 13.70. LC-MS m/z calcd. C$_{22}$H$_{26}$N$_4$O$_5$: theoretical value: 426.19 [M+H]$^+$, experimental value: 426.19. Anal. Calcd. C$_{22}$H$_{26}$N$_4$O$_5$:(426.19) theoretical value: C: 61.96, N: 13.14, H: 6.15, experimental value: C: 61.61, N: 12.75, H: 6.15.

The above preparation method can be expressed as follows:

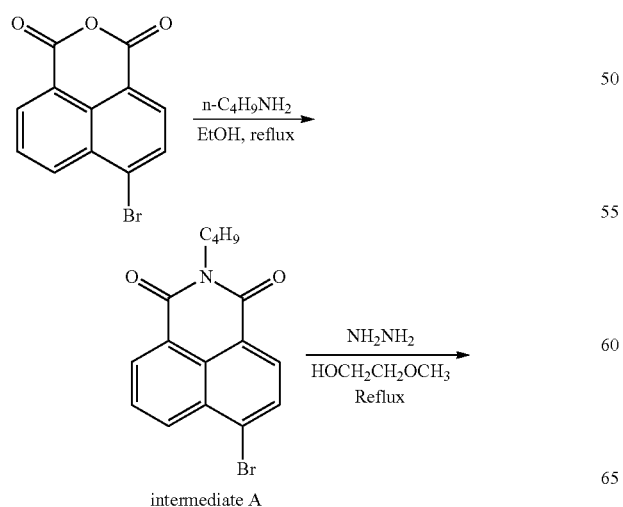

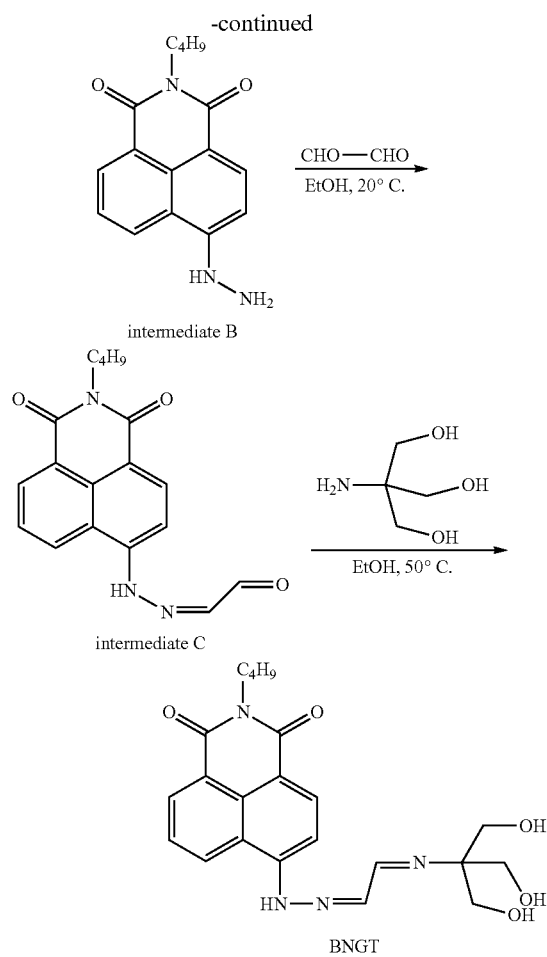

Example 5: Selectivity and Sensitivity of BNGT to Cu$^{2+}$

Adding Fe$^{3+}$, K$^+$, Na$^+$, Mg$^{2+}$, Ni$^{2+}$, Ag$^+$, Cr$^{3+}$, Cd$^{2+}$, Co$^{2+}$, Zn$^{2+}$, Mn$^{2+}$, Fe$^{2+}$, Cu$^{2+}$, Ca$^{2+}$, Hg$^{2+}$ and Pb$^{2+}$ respectively to the acetonitrile/water (in a volume ratio of 1/99) solution of BNGT, and obtaining the fluorescence spectrum before and after the addition of metal ions, with the results as shown in FIG. 1; solvent: acetonitrile/water (in a volume ratio of 1/99); concentration: BNGT 10 μm, metal ions 100 μm; excitation wavelength: 345 nm; slot width: 5 nm; temperature: 25° C. It can be seen that only $Cu^{2+}$ could enhance the fluorescence intensity of the BNGT solution, which was 9.2 times stronger at a wavelength of 392 nm and 9.4 times stronger at a wavelength of 754 nm; the bright blue could be seen under a UV lamp, indicating that BNGT in acetonitrile/water (in a volume ratio of 1/99) could have high selectivity and sensitivity to $Cu^{2+}$ by using two wavelengths, and did not respond to other individual metals.

Example 6: Linear Range and Detection Limit of $Cu^{2+}$ Detected by BNGT

Figure 2:
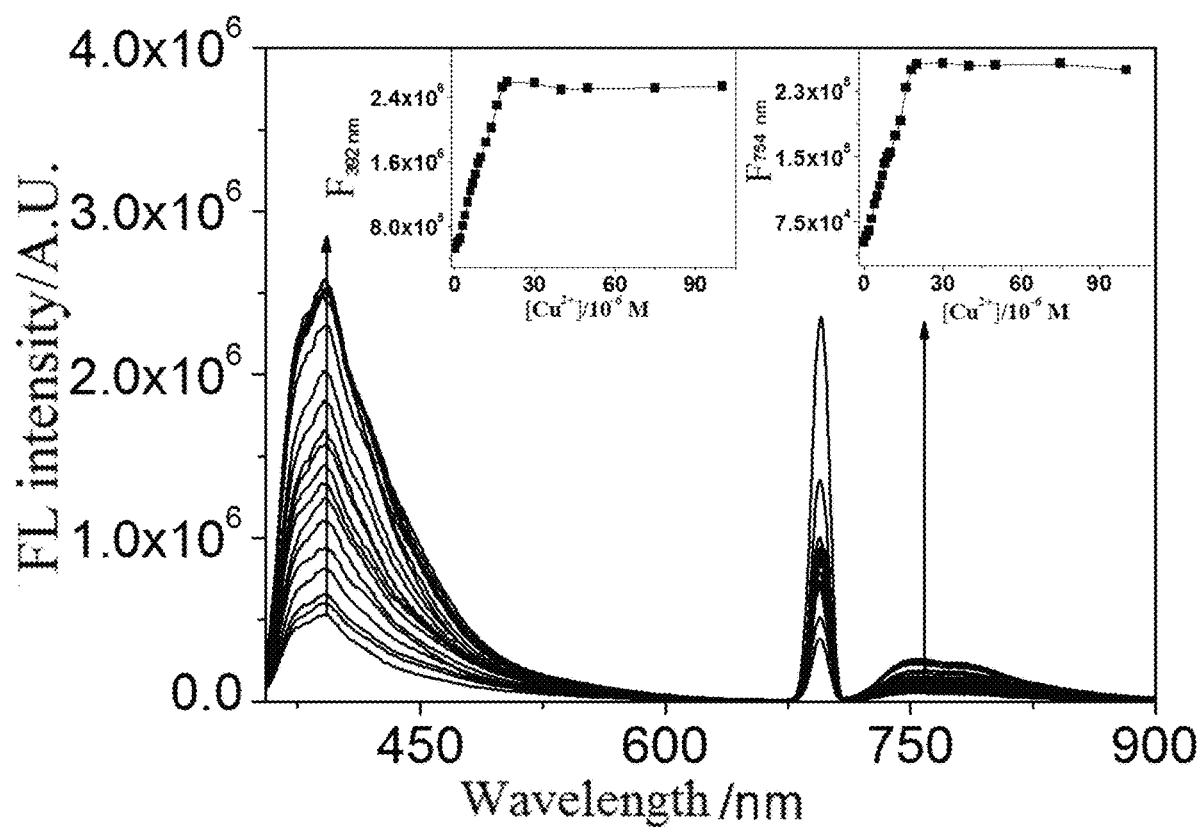
FIG. 2 shows the fluorescence spectrum of a BNGT solution (10 μM) with different concentrations of $Cu^{2+}$.

FIG. 2 shows the fluorescence spectrum of a BNGT solution (with acetonitrile/water as the solvent in a volume ratio of 1/99) with different concentrations of $Cu^{2+}$; excitation wavelength: 345 nm; slot width: 5 nm; temperature: 25° C.; concentrations of $Cu^{2+}$ from bottom to top: 0, 1, 2, 3, 4, 5, 6, 7, 8, 9, 10, 12, 14, 16, 18, 20, 30, 40, 50, 75 and 100 μM. The insets show the relationship between the maximum fluorescence intensity of the BNGT solution and the concentration of $Cu^{2+}$ at 392 nm and 754 nm, respectively. As can be seen from FIG. 2, when the concentration of $Cu^{2+}$ was in the range of 0 to 20 μM, the fluorescence intensity of BNGT at wavelengths of 392 nm and 754 nm had a good linear relationship with the concentration of $Cu^{2+}$, the linear equations being $F=109170.7529 \times [Cu^{2+}]+530079.7583$ and $F=10677.1606 \times [Cu^{2+}]+50519.5202$, the correlation coefficients being $R=0.9928$ and $R=0.9930$, respectively. According to atitration experiments and blank experiments at 392 nm and 754 nm, the detection limit of BNGT for $Cu^{2+}$ was $2.6368 \times 10^{-7}$ mol/L and $2.0156 \times 10^{-7}$ mol/L, respectively, indicating that BNGT could perform quantitative detection for $Cu^{2+}$ with a high selectivity and a high sensitivity by using two wavelengths.

Example 7: Effects of Coexisting Ions on Detection of $Cu^{2+}$ by BNGT

Figure 3:
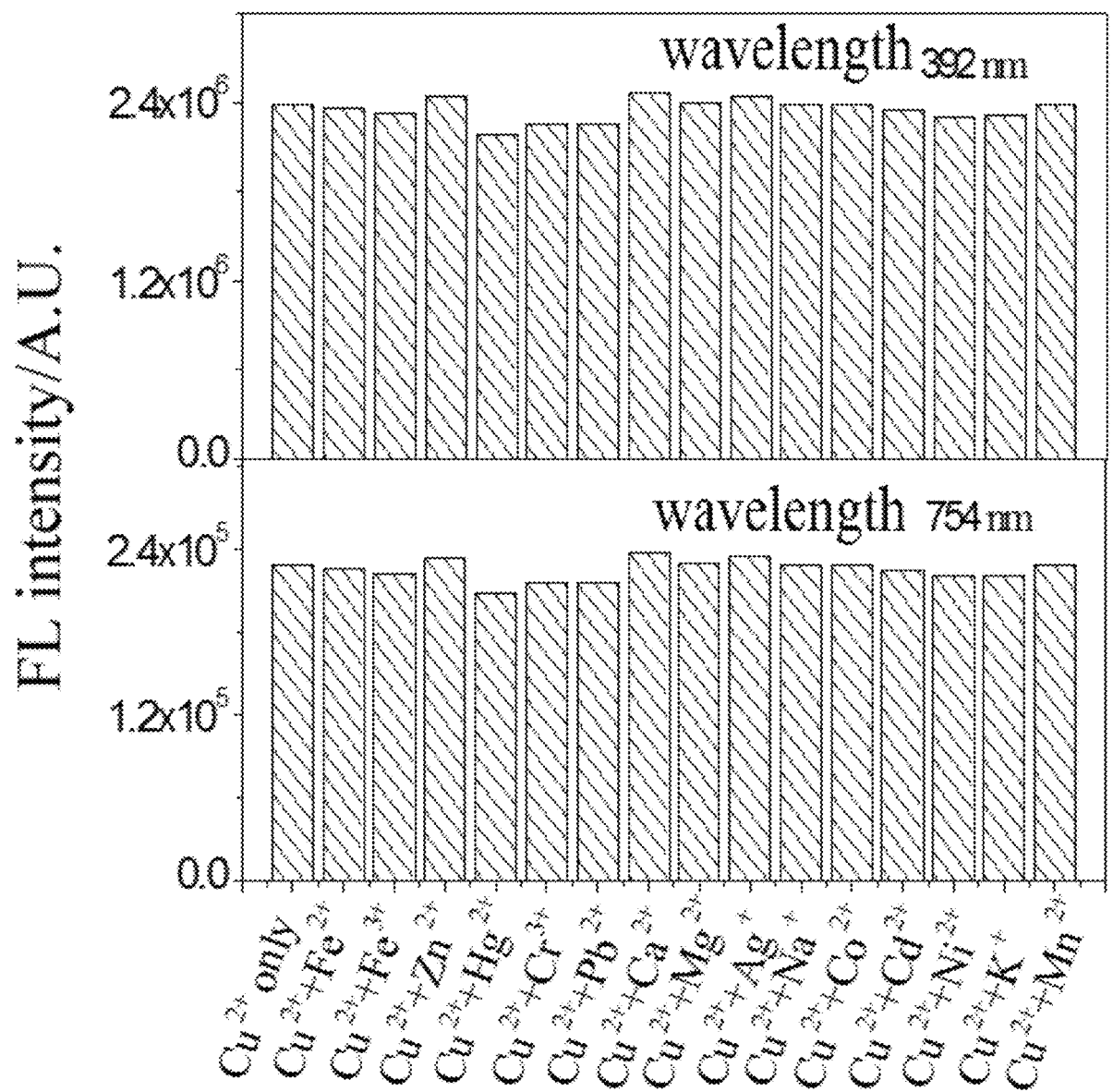
FIG. 3 shows the effect of coexisting metal ions on the fluorescence intensity of a BNGT solution containing $Cu^{2+}$.

FIG. 3 shows the effect of environmentally and biologically relevant metal ions on the maximum fluorescence intensity of a BNGT solution (with acetonitrile/water as the solvent in a volume ratio of 1/99) containing $Cu^{2+}$ at 392 nm and 754 nm; solvent: acetonitrile/water (in a volume ratio of 1/99); concentration: BNGT 10 μM; metal ions 100 μM; excitation wavelength: 345 nm; slit width: 5 nm; temperature: 25° C. It can be seen that the addition of $Mg^{2+}$, $K^+$, $Na^+$, $Ag^+$, $Cr^{3+}$, $Cd^{2+}$, $Co^{2+}$, $Zn^{2+}$, $Mn^{2+}$, $Fe^{2+}$, $Fe^{3+}$, $Ca^{2+}$, $Pb^{2+}$ and $Hg^{2+}$ (100 μM) had little effect on the maximum fluorescence intensity of the solution. The results show that BNGT in acetonitrile/water in a volume ratio of 1/99 had strong anti-interference ability in detecting $Cu^{2+}$.

Example 8: Analysis of $Cu^{2+}$ in Spiked Water Samples

In order to investigate the practicality of BNGT in the actual environment, BNGT was used to carry out the spiked analysis of the pond water and tap water of Dushu Lake Campus of Soochow University. The specific implementation method of the detection was as follows: Taking respectively 1 mL of the sample to be tested, adding 100 μL of 1 mM BNGT solution with acetonitrile as the solvent, then respectively adding 15 μM and 20 μM $Cu^{2+}$, and making up to volume with deionized water to obtain the solution to be tested in acetonitrile/water (in a volume ratio of 1/99) with the concentration of BNGT at 10 μM; exciting at a slit width of 5 nm with 345 nm as the excitation wavelength, and measuring the fluorescence spectrum of the solution; and obtaining the concentration of $Cu^{2+}$ in the water sample to be measured according to the linear relationship between the maximum fluorescence intensity of BNGT and the concentration of $Cu^{2+}$ (as shown in the inset in FIG. 2). The results were shown in Table 2. The concentration of $Cu^{2+}$ measured at 392 nm and 754 nm was close to the concentration of $Cu^{2+}$ added in the system, the recovery rate of $Cu^{2+}$ was between 97.13% and 103.45%, and the relative standard deviation of the three parallel experiments was less than 1.58%. Therefore, BNGT could be used to effectively detect $Cu^{2+}$ in actual environmental water samples by means of two wavelengths.

TABLE 2

Recovery rate of $Cu^{2+}$ in pond water and tap water (3 parallel determinations)

| Sample | Added $Cu^{2+}$ | Wavelength 392 nm | | | Wavelength 754 nm | | |
|---|---|---|---|---|---|---|---|
| | | Detected $Cu^{2+}$ | Recovery rate (%) | Relative standard deviation (%) | Detected $Cu^{2+}$ | Recovery rate (%) | Relative standard deviation (%) |
| Pond water | 15 | 14.77 | 98.47 | 0.59 | 14.57 | 97.13 | 1.10 |
| | 20 | 20.69 | 103.45 | 0.72 | 20.13 | 100.65 | 0.71 |
| Tap water | 15 | 14.96 | 99.73 | 1.00 | 14.80 | 98.67 | 1.35 |
| | 20 | 20.31 | 101.55 | 1.58 | 20.40 | 102.00 | 0.66 |

Solvent: acetonitrile/water (in a volume ratio of 1/99); concentration: BNGT 10 μM; concentration unit of $Cu^{2+}$: $10^{-6}$ mol/L.

The compound designed and synthesized by the present invention is relatively easy to synthesize, can detect $Cu^{2+}$ with a good selectivity and a high sensitivity by means of two wavelengths and enhanced fluorescence, can be applied to almost-all-water systems, and has good practicability and a bright application prospective.

Example 9: Response of BNGT to pH

Preparing a $1.0 \times 10^{-3}$ mol/L BNGT stock solution with acetonitrile as a solvent, and transferring 100 μL of the BNGT stock solution respectively into three series of 10 mL volumetric flasks; adding 7 mL of deionized water to the first series of volumetric flasks, adding 2 mL of deionized water and 5 ml of acetonitrile to the second series of volumetric flasks, and adding 1 mL of deionized water and 8 ml of acetonitrile to the third series of volumetric flasks; then titrating to the desired pH value respectively with 0.1 M NaOH and 0.1 M HCl aqueous solutions, and finally making up to volume with deionized water to obtain an acetonitrile/water solution of BNGT with different pHs in three solvent systems, the volume ratios of acetonitrile/water in the three solvent systems being 1/99, 1/1 and 8/2, respectively.

Figure 4:
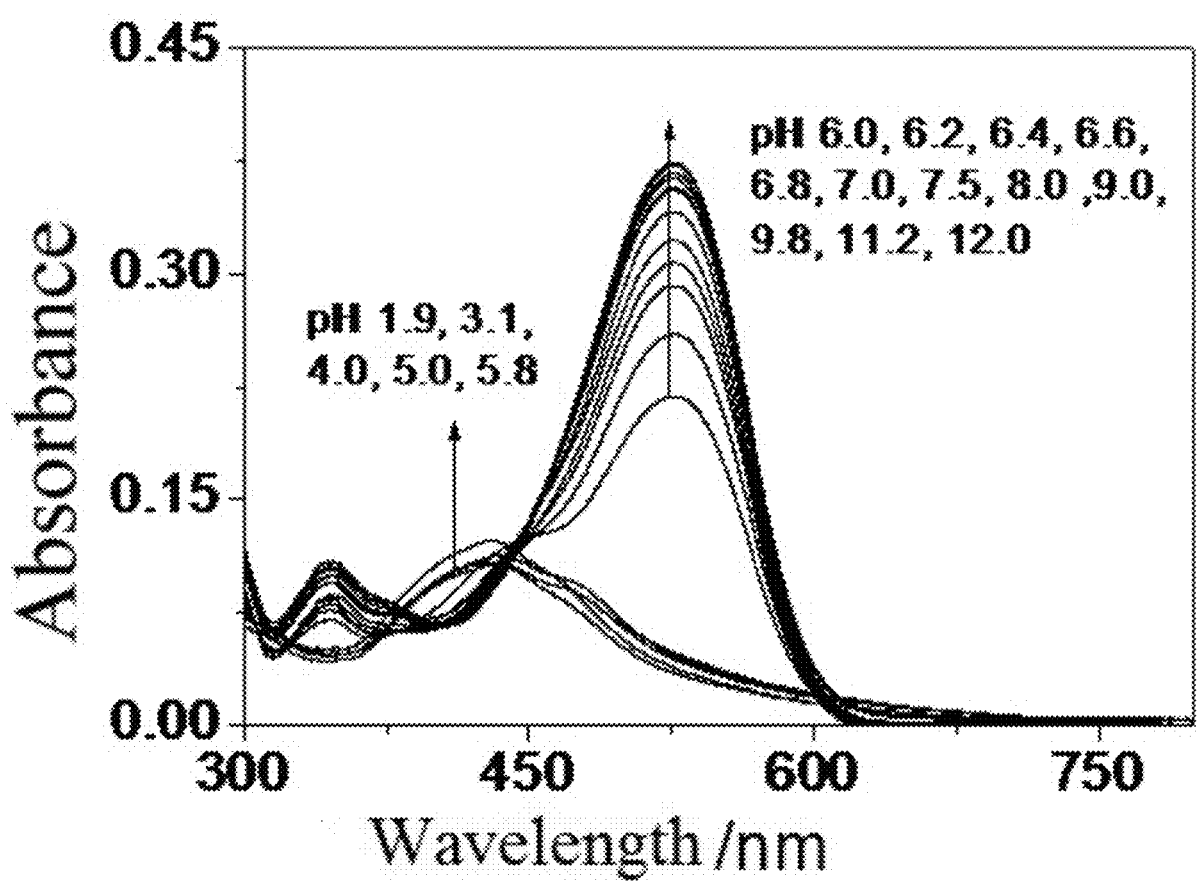
FIG. 4 shows the UV-Vis absorption spectrum of BNGT at different pHs.
Figure 5:
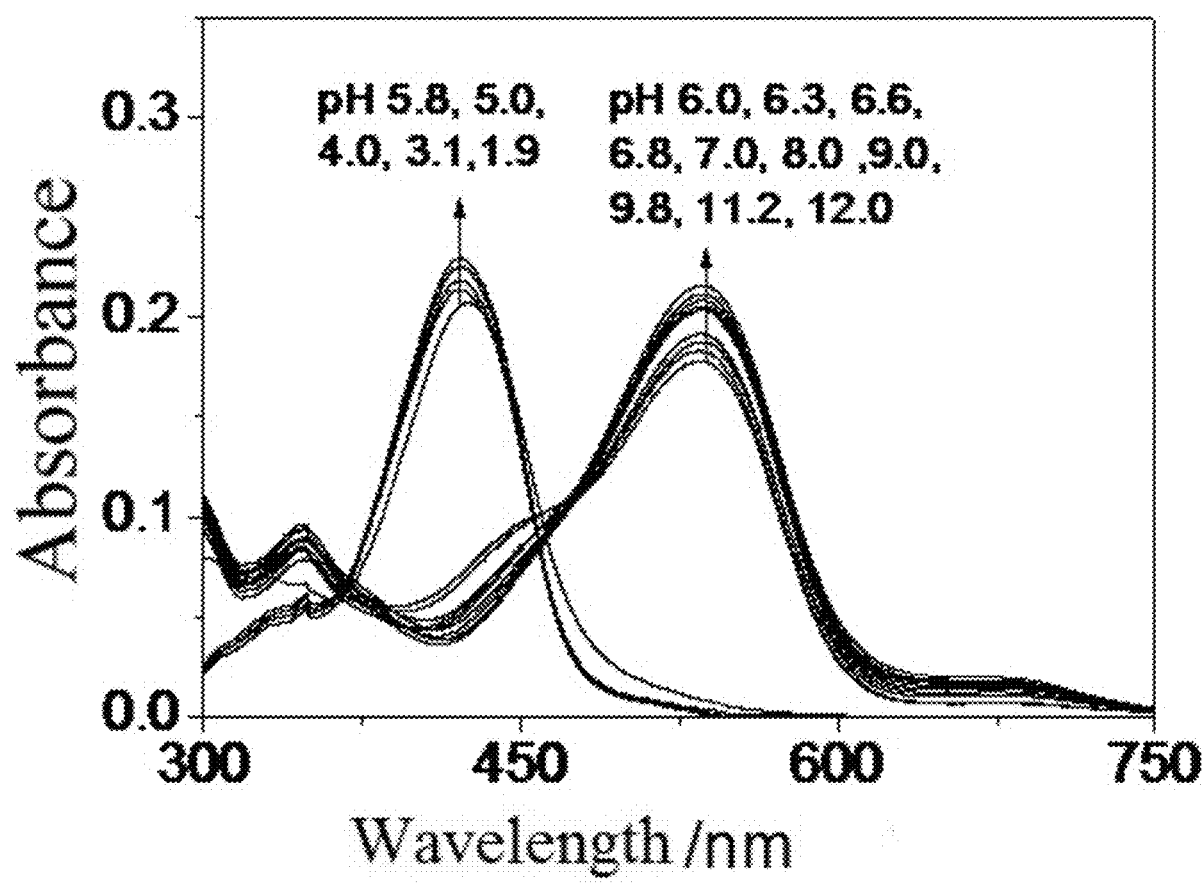
FIG. 5 shows the UV-Vis absorption spectrum of BNGT at different pHs.
Figure 6:
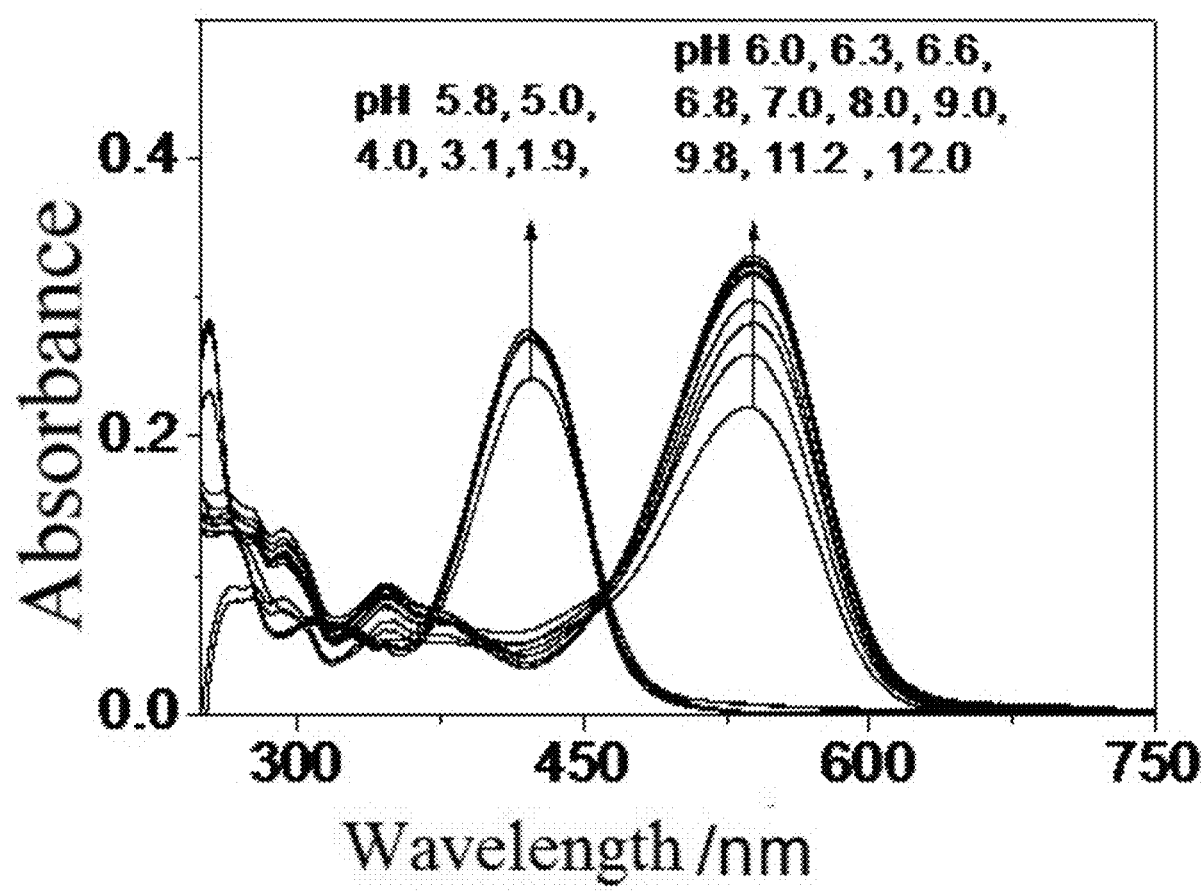
FIG. 6 shows the UV-Vis absorption spectrum of BNGT at different pHs.

The responses of UV-Vis absorption spectra of BNGT (with acetonitrile/water as the solvent in a volume ratio of 1/99, 1/1 and 8/2) to different pHs were investigated, respectively, as shown in FIGS. 4, 5 and 6.

FIG. 4 shows the UV-Vis absorption spectrum of BNGT (with acetonitrile/water as the solvent in a volume ratio of 1/99) in a pH range of 1.9 to 12.0; solvent: acetonitrile/water (in a volume ratio of 1/99); concentration: BNGT 10 µM; pH: 1.9, 3.1, 4.0, 5.0, 5.8, 6.0, 6.2, 6.4, 6.6, 6.8, 7.0, 7.5, 8.0, 9.0, 9.8, 11.2, 12.0. As can be concluded from the figure, when the pH was in the range of 1.9 to 5.8, the maximum absorption wavelength of BNGT was around 432 nm, and the absorbance was at a low level; when the pH was in the range of 6.0 to 12.0, the maximum absorption wavelength was about 527 nm, and the absorbance increased significantly; when pH changed from 5.8 to 6.0, the solution changed from colorless to red, and the maximum absorption wavelength and absorbance changed suddenly, the maximum wavelength red-shifting by 95 nm, the absorbance at 527 nm increasing by about 6 times.

FIG. 5 shows the UV-Vis absorption spectrum of BNGT (with acetonitrile/water as the solvent in a volume ratio of 1/1) at different pHs; solvent: acetonitrile/water (in a volume ratio of 1/1); concentration: BNGT 10 µM; pH: 1.9, 3.1, 4.0, 5.0, 5.8, 6.0, 6.3, 6.6, 6.8, 7.0, 8.0, 9.0, 9.8, 11.2, 12.0. As can be seen from the figure, when the pH was in the range of 1.9 to 5.8, the maximum absorption wavelength of BNGT was around 420 nm; when the pH was in the range of 6.0 to 12.0, the maximum absorption wavelength was around 535 nm; when pH changed from 5.8 to 6.0, the solution changed from colorless to red, and the maximum absorption wavelength and absorbance changed suddenly, the maximum absorption wavelength red-shifting by 115 nm, the absorbance at 535 nm increasing by about 20 times.

FIG. 6 shows the UV-Vis absorption spectrum of BNGT (with acetonitrile/water as the solvent in a volume ratio of 8/2) at different pHs; solvent: acetonitrile/water (in a volume ratio of 8/2); concentration: BNGT 10 µM; pH: 1.9, 3.1, 4.0, 5.0, 5.8, 6.0, 6.3, 6.6, 6.8, 7.0, 8.0, 9.0, 9.8, 11.2, 12.0. As can be seen from the figure, when the pH was in the range of 1.9 to 5.8, the maximum absorption wavelength of BNGT was around 422 nm; when the pH was in the range of 6.0 to 12.0, the maximum absorption wavelength was around 537 nm; when pH changed from 5.8 to 6.0, the solution changed from colorless to red, and the maximum absorption wavelength and absorbance changed suddenly, the maximum absorption wavelength red-shifting by 115 nm, the absorbance at 537 nm increasing by about 28 times.

Figure 7:
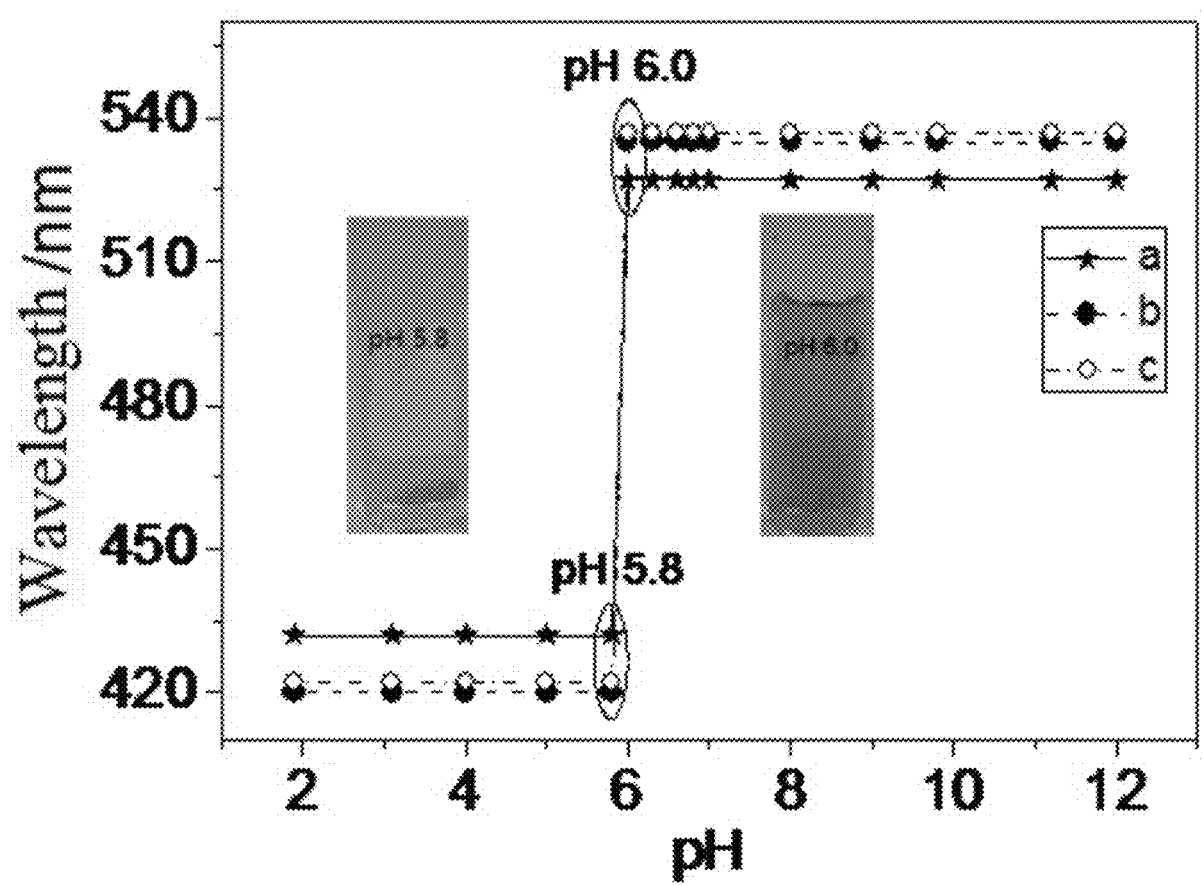
FIG. 7 shows the maximum absorption wavelength and color of BNGT at different pHs.

As can be seen, in a very narrow pH range (pH 5.8 to 6.0), all the BNGT solutions with acetonitrile/water as the solvent in three different volume ratios had obvious sudden change in maximum absorption wavelength and striking color change, as shown in FIG. 7; solvent: acetonitrile/water, in a volume ratio of 1/99 (a), 1/1 (b) and 8/2 (c); concentration: BNGT 10 µM; pH: 1.9, 3.1, 4.0, 5.0, 5.8, 6.0, 6.3, 6.6, 6.8, 7.0, 8.0, 9.0, 9.8, 11.2, 12.0; the absorbance at 527 nm, 535 nm and 537 nm increased significantly. Therefore, in the three solvents (acetonitrile/water in a volume ratio of 1/99, 1/1 and 8/2), BNGT could be used as a pH colorimetric switch by means of three ways (a maximum absorption wavelength, absorbance and color).

Example 10: Speed of Response of BNGT to pH

Figure 8:
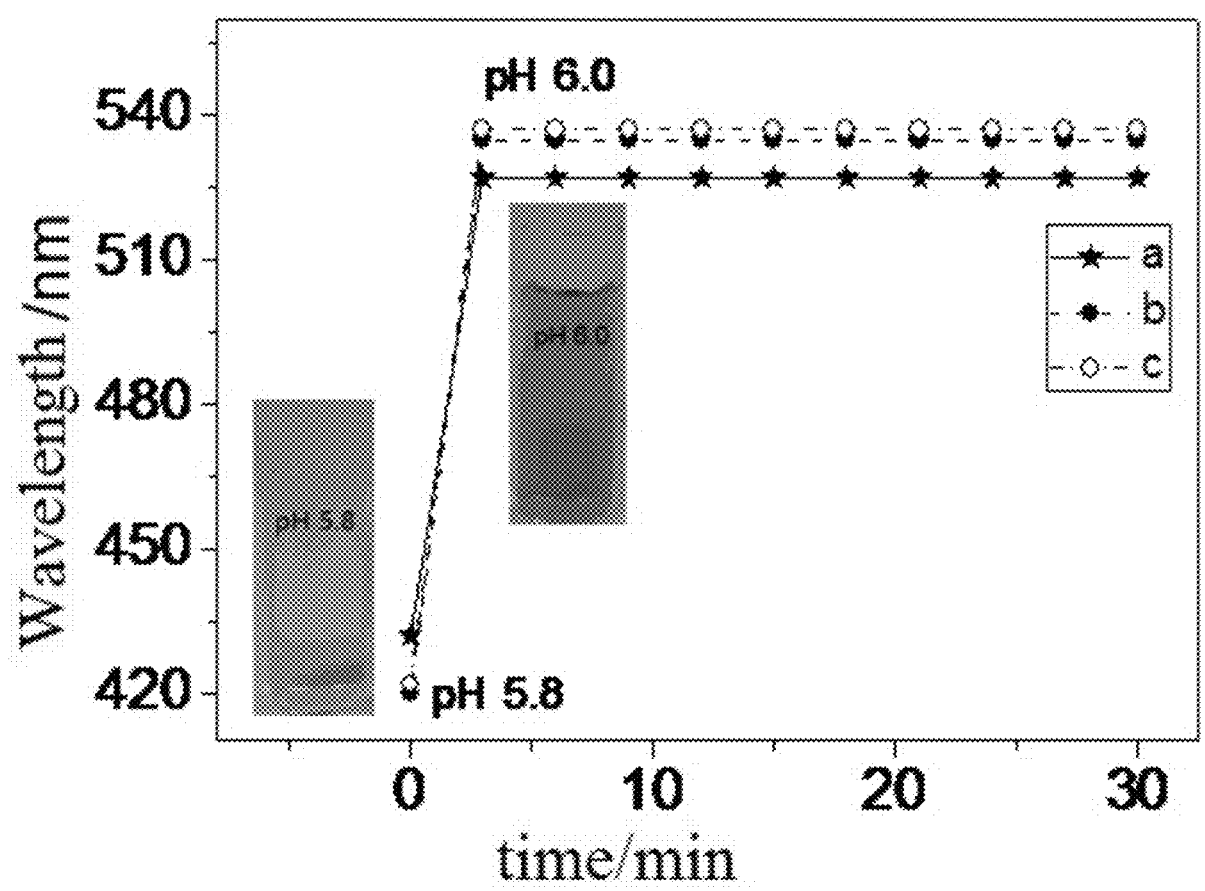
FIG. 8 shows the speed of response of the maximum absorption wavelength and color of BNGT to pH.

To investigate the speed of response of BNGT to pH, adding 1 M NaOH aqueous solution to an acetonitrile/water (in a volume ratio of 1/99 (a), 1/1 (b) and 8/2 (c)) solution of BNGT at pH 5.8 to adjust the pH to 6.0; measuring the UV-Vis absorption spectrum of the solution before and after the adjustment, and plotting the maximum absorption wavelength and color over time, with the results as shown in FIG. 8; solvent: acetonitrile/water, in a volume ratio of 1/99 (a), 1/1 (b) and 8/2 (c); concentration: BNGT 10 µM. As can be seen from FIG. 8, when the pH changed from 5.8 to 6.0, the maximum absorption wavelengths of the three BNGT solutions quickly changed from 432 nm, 420 nm and 422 nm to 527 nm, 535 nm and 537 nm, respectively, and the color immediately changed from colorless to red.

Figure 9:
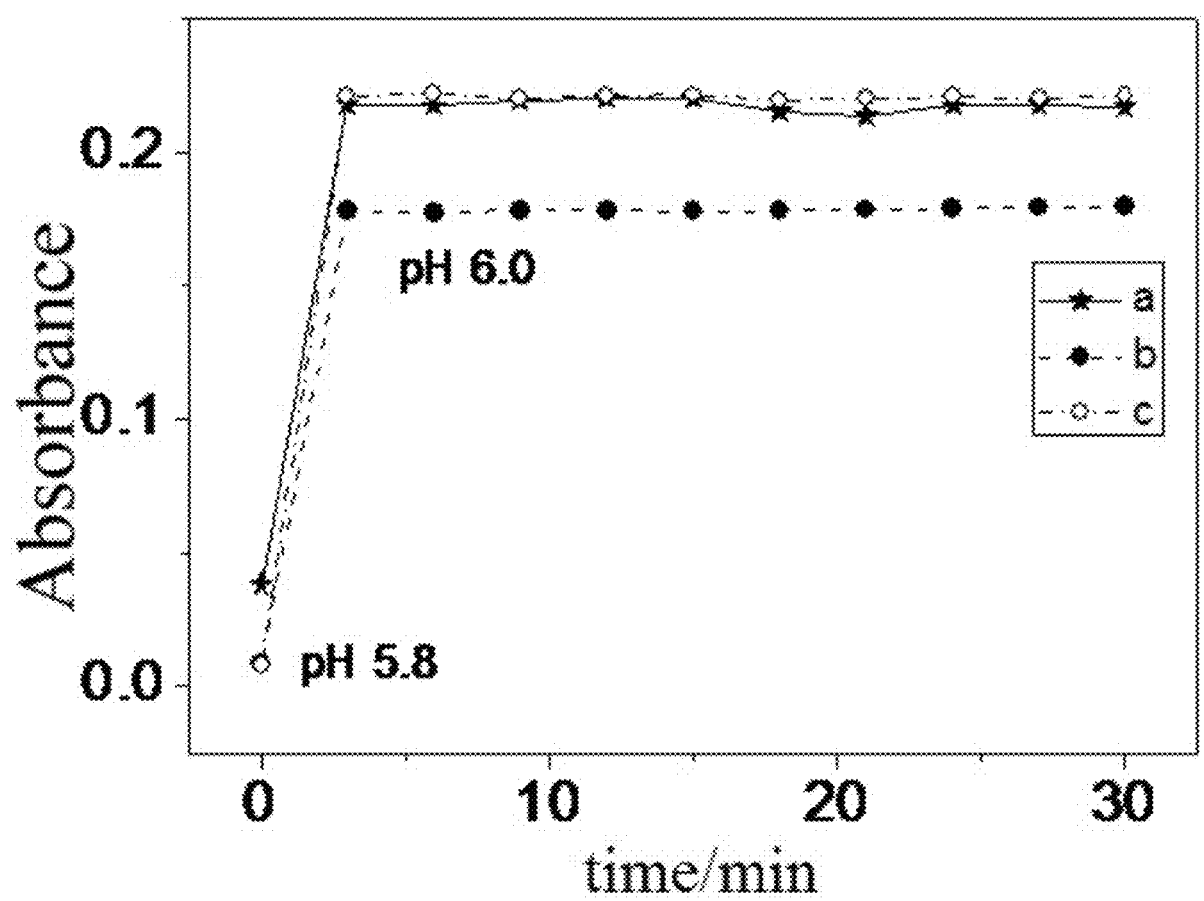
FIG. 9 shows the speed of response of the absorbance of BNGT to pH.

The absorbance was plotted against time and the results were shown in FIG. 9; solvent: acetonitrile/water, in a volume ratio of 1/99 (a), 1/1 (b) and 8/2 (c); concentration: BNGT 10 µM; absorption wavelength: 527 nm, 535 nm and 537 nm. As can be seen from FIG. 9, after the addition of the NaOH aqueous solution to the acetonitrile/water (in a volume ratio of 1/99 (a), 1/1 (b) and 8/2 (c)) solution of BNGT, the absorbance at 527 nm, 535 nm and 537 nm reached the maximum in about 2 min and remained basically stable for the next 30 min.

Therefore, in the three solvents (acetonitrile/water in a volume ratio of 1/99, 1/1 and 8/2), BNGT could rapidly respond to pH as a pH colorimetric switch by means of three ways (a maximum absorption wavelength, absorbance and color).

Example: 11: Effect of Coexisting Ions on BNGT as a pH Colorimetric Switch

In order to understand the interference of common metal ions on BNGT as a pH colorimetric switch, $Fe^{2+}$, $Fe^{3+}$, $Cu^{2+}$, $K^+$, $Na^+$, $Mg^{2+}$, $Ag^+$, $Zn^{2+}$, $Cr^{3+}$, $Cd^{2+}$, $Co^+$, $Ni^{2+}$, $Mn^{2+}$, $Pb^{2+}$, $Hg^{2+}$ and $Ca^{2+}$ were added to the acetonitrile/water (in a volume ratio of 1/99 (a), 1/1 (b) and 8/2 (c)) solution, and the UV-Vis absorption spectra of the solution before and after the addition of these metal ions were obtained.

Figure 10:
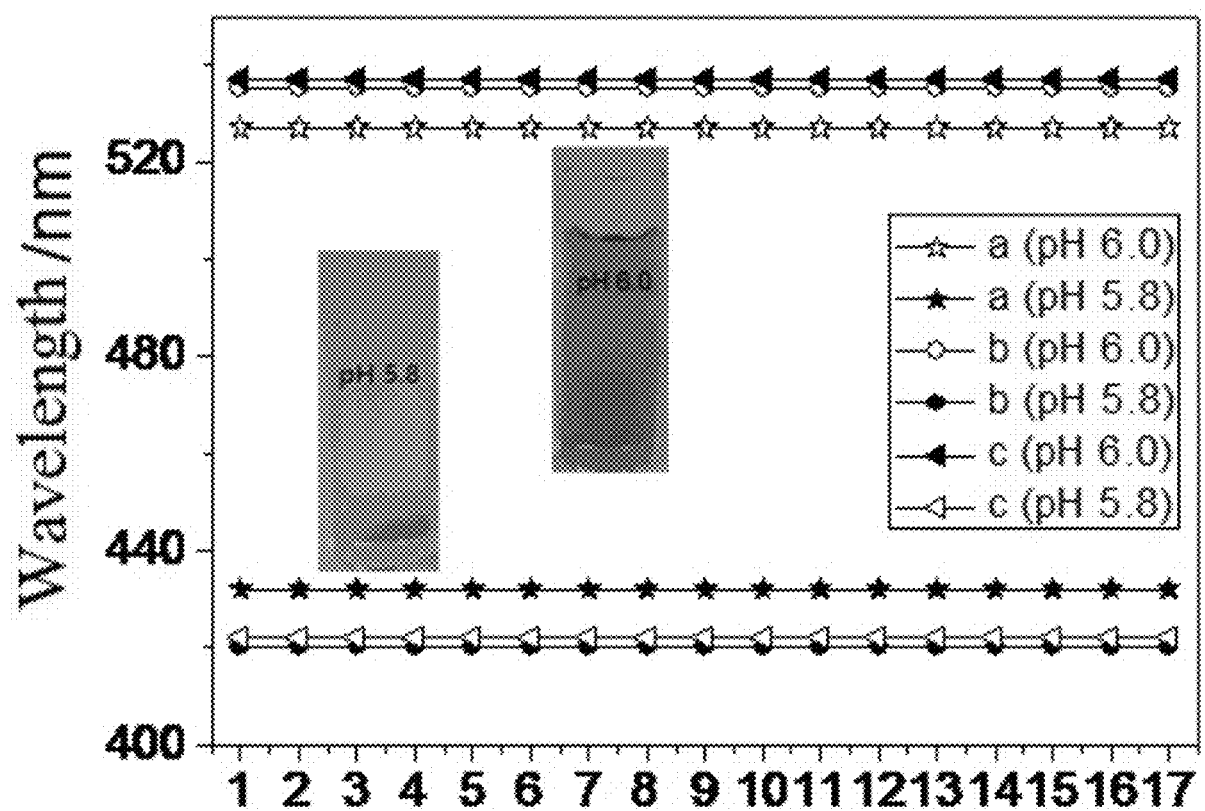
FIG. 10 shows the effect of coexisting metal ions on the maximum absorption wavelength and color of the BNGT solution.

First, the effect of coexisting metal ions on the maximum absorption wavelength and color of the solution was examined, with the results as shown in FIG. 10; solvent: acetonitrile/water, in a volume ratio of 1/99 (a), 1/1 (b) and 8/2 (c); concentration: BNGT 10 µM, metal ions 100 µM; 1: none, 2: $Ca^{2+}$, 3: $Mg^{2+}$, 4: $Ag^+$, 5: $Pb^{2+}$, 6: $Cu^{2+}$, 7: $Mn^{2+}$, 8: $Co^{2+}$, 9: $Cd^{2+}$, 10: $Ni^{2+}$, 11: $K^+$, 12: $Na^+$, 13: $Fe^{2+}$, 14: $Zn^{2+}$, 15: $Cr^{2+}$, 16: $Hg^{2+}$, 17: $Fe^{2+}$. As can be seen from FIG. 10, the maximum absorption wavelength and color of the solutions at pH 5.8 and pH 6.0 before and after the addition of metal ions were almost unchanged. Therefore, the response of BNGT to pH in terms of the maximum absorption wavelength and color was hardly affected by the aforementioned metal ions.

Figure 11:
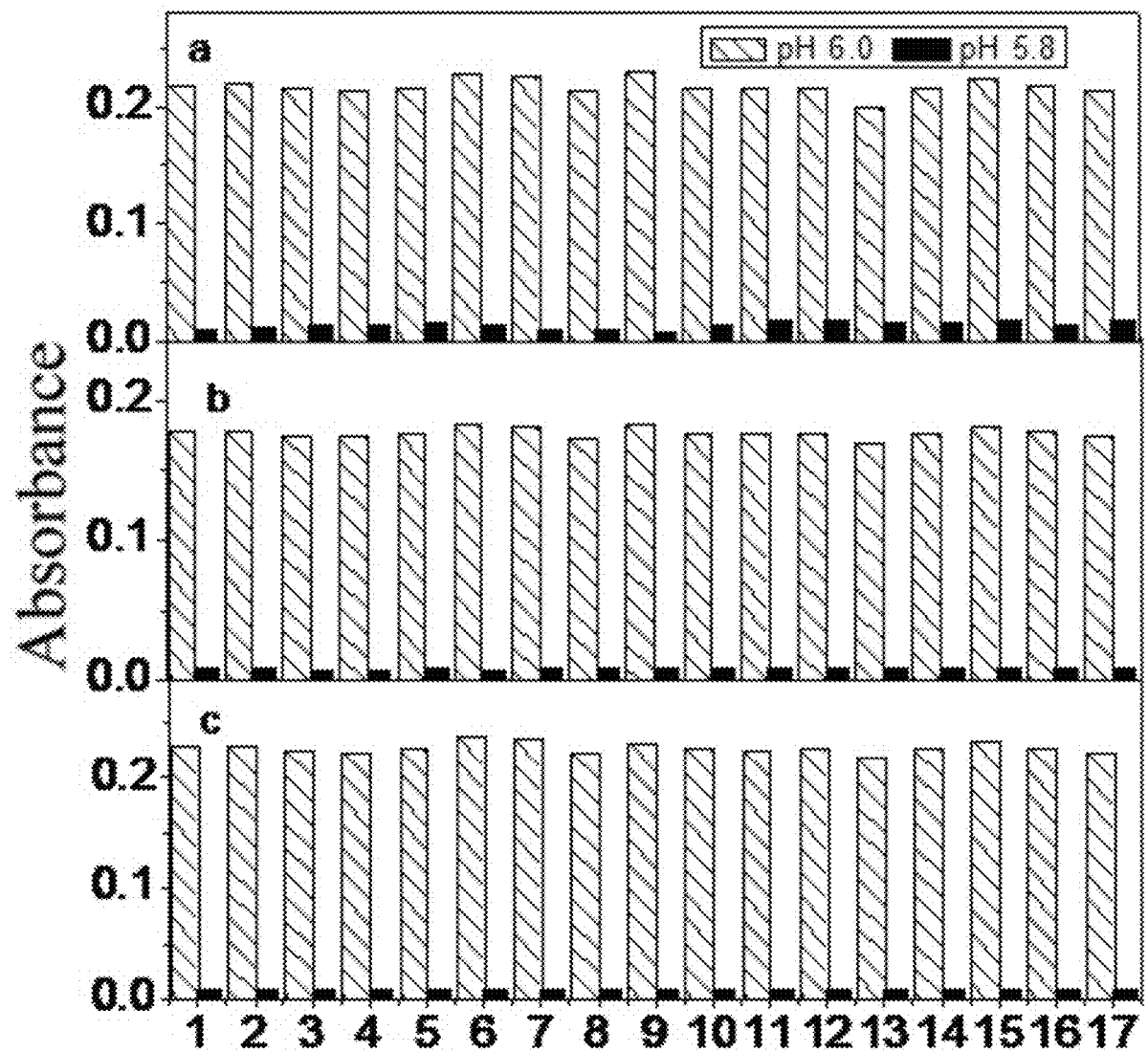
FIG. 11 shows the effect of coexisting metal ions on the absorbance of the BNGT solution.

Second, the effect of coexisting metal ions on the absorbance of the solution at 527 nm, 535 nm and 537 nm was investigated, with the results as shown in FIG. 11; solvent: acetonitrile/water, in a volume ratio of 1/99 (a), 1/1 (b) and 8/2 (c); concentration: BNGT 10 µM, metal ions 100 µM; 1: none, 2: $Ca^{2+}$, 3: $Mg^{2+}$, 4: $Ag^+$, 5: $Pb^{2+}$, 6: $Cu^{2+}$, 7: $Mn^{2+}$, 8: $Co^{2+}$, 9: $Cd^{2+}$, 10: $Ni^{2+}$, 11: $K^+$, 12: $Na^+$, 13: $Fe^{3+}$, 14: $Zn^{2+}$, 15: $Cr^{2+}$, 16: $Hg^{2+}$, 17: $Fe^{2+}$; absorption wavelength:

527 nm, 535 nm and 537 nm. It can be seen from FIG. 11 that the absorbance of the solutions at pH 5.8 and pH 6.0 did not change much at 527 nm, 535 nm and 537 nm before and after the addition of the metal ions. Therefore, the aforementioned metal ions had little effect on the response of BNGT to pH in terms of enhanced absorbance.

Therefore, in the three solvents (acetonitrile/water in a volume ratio of 1/99, 1/1 and 8/2), BNGT had good anti-interference as a pH colorimetric switch by means of three ways (a maximum absorption wavelength, absorbance and color).

Example: 12: Reversibility of BNGT as a pH Colorimetric Switch

1 M HCl and 1 M NaOH were used to make the pH value of the acetonitrile/water (in a volume ratio of 1/99 (a), 1/1 (b) and 8/2 (c)) solution of BNGT alternately change between 5.8 and 6.0, so as to determine the UV-Vis absorption spectrum of the solution.

Figure 12:
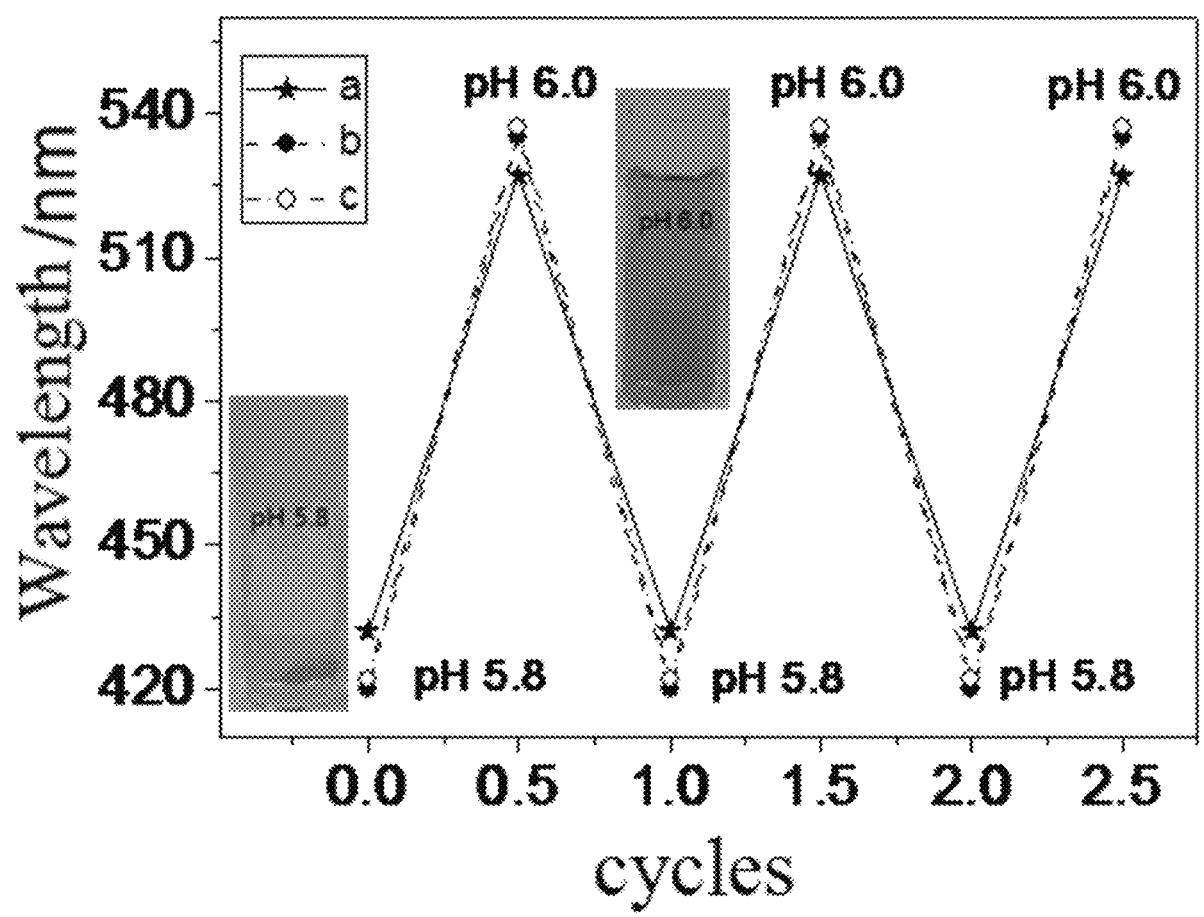
FIG. 12 shows the reversibility of response of the maximum absorption wavelength and color of BNGT to pH.

First, the reversibility of response of the maximum absorption wavelength and color of the solution to pH was investigated, with the results as shown in FIG. 12; solvent: acetonitrile/water, in a volume ratio of 1/99 (a), 1/1 (b) and 8/2 (c); concentration: BNGT 10 µM. As can be seen from FIG. 12, when the pH value was 5.8, the system was colorless and the absorption wavelength was small; when the pH value was 6.0, the system was red and the absorption wavelength was large. Therefore, among the three solvents, BNGT had good reversibility of response to pH in terms of the maximum absorption wavelength and color.

Figure 13:
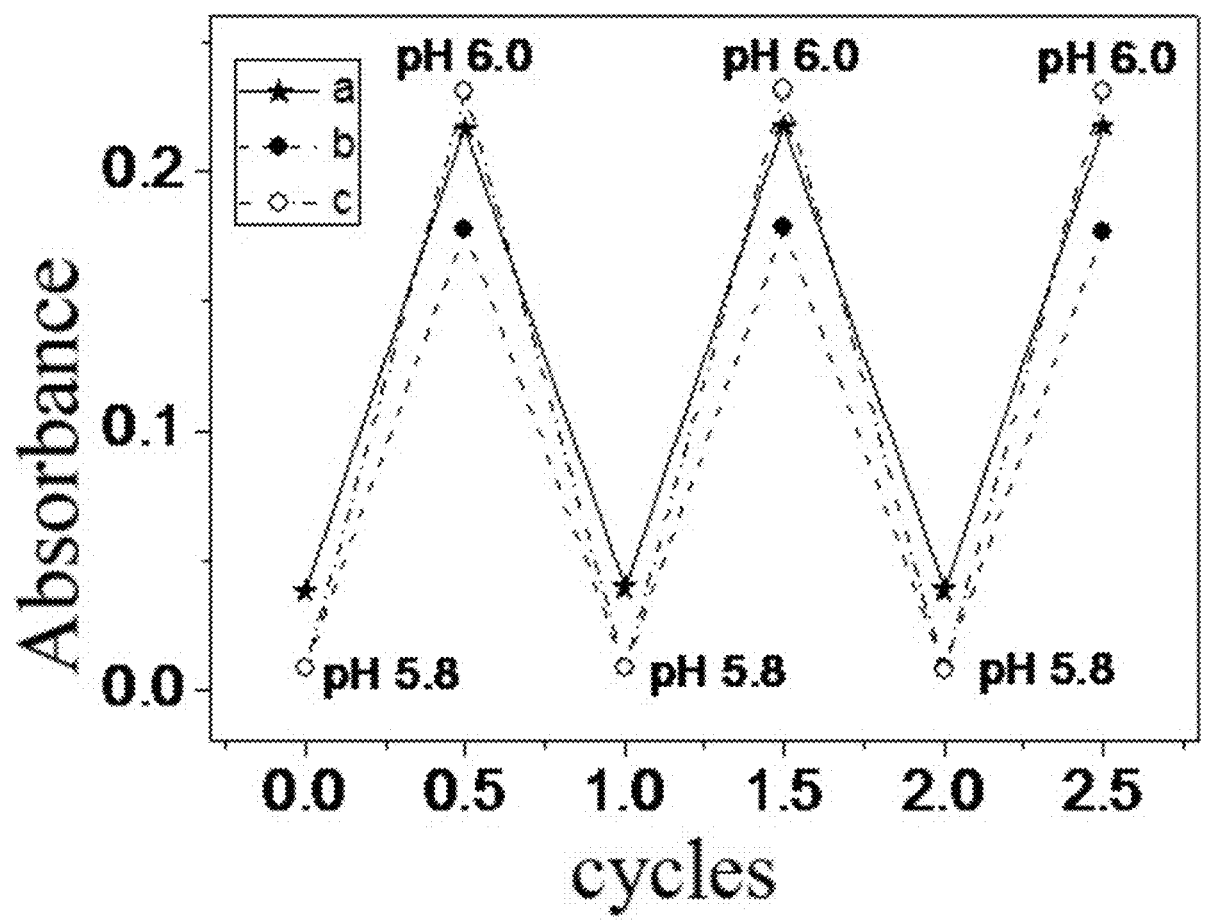
FIG. 13 shows the reversibility of response of the absorbance of BNGT to pH.

Second, the reversibility of response of the absorbance of BNGT to pH at 527 nm, 535 nm and 537 nm was investigated, with the results as shown in FIG. 13; solvent: acetonitrile/water, in a volume ratio of 1/99 (a), 1/1 (b) and 8/2 (c); concentration: BNGT 10 µM; the maximum absorption wavelengths corresponding to the absorbance of the three solutions were 527 nm, 535 nm and 537 nm, respectively. It can be seen from the figure that the pH value alternated between 5.8 and 6.0, and the absorbance of the acetonitrile/water (in a volume ratio of 1/99 (a), 1/1 (b) and 8/2 (c)) solution of BNGT also changed circularly from small to large at 527 nm, 535 nm and 537 nm, respectively. It can be seen that the absorbance of BNGT at 527 nm, 535 nm and 537 nm also had very good reversibility of response to pH.

Therefore, in the three solvents (acetonitrile/water in a volume ratio of 1/99, 1/1 and 8/2), BNGT had good reversibility as a pH colorimetric switch by means of three ways (a maximum absorption wavelength, absorbance and color). The present invention designs and synthesizes a novel 1,8-naphthalimide derivative BNGT, which is relatively easy to prepare, can be used as a sensitive, responsive, and reversible three-way pH colorimetric switch, and can be especially applied to almost-all-water systems.

The invention claimed is:

1. A preparation method for a 1,8-naphthalimide derivative, comprising the following steps:
   (1) preparing an intermediate A using 4-bromo-1,8-naphthalic anhydride and n-butylamine as raw materials;
   (2) preparing an intermediate B using the intermediate A and hydrazine hydrate as raw materials;
   (3) preparing an intermediate C using the intermediate B and glyoxal as raw materials; and
   (4) preparing the 1,8-naphthalimide derivative using the intermediate C and trihydroxymethyl aminomethane as raw materials.

2. A preparation method for a $Cu^{2+}$ fluorescent probe system, comprising the following steps:
   (1) preparing an intermediate A using 4-bromo-1,8-naphthalic anhydride and n-butylamine as raw materials;
   (2) preparing an intermediate B using the intermediate A and hydrazine hydrate as raw materials;
   (3) preparing an intermediate C using the intermediate B and glyoxal as raw materials;
   (4) preparing a 1,8-naphthalimide derivative using the intermediate C and trihydroxymethyl aminomethane as raw materials; and
   (5) adding the 1,8-naphthalimide derivative to a solvent to prepare the $Cu^{2+}$ fluorescent probe system, the solvent being an organic solvent and/or water.

3. A method for detecting the content of $Cu^{2+}$ in the system, comprising the following steps:
   (1) preparing an intermediate A using 4-bromo-1,8-naphthalic anhydride and n-butylamine as raw materials;
   (2) preparing an intermediate B using the intermediate A and hydrazine hydrate as raw materials;
   (3) preparing an intermediate C using the intermediate B and glyoxal as raw materials;
   (4) preparing a 1,8-naphthalimide derivative using the intermediate C and trihydroxymethyl aminomethane as raw materials; and
   (5) adding the 1,8-naphthalimide derivative solution to the system, measuring fluorescence intensity, and then determining the content of $Cu^{2+}$ in the system according to a curve of relationship between the fluorescence intensity and a concentration of $Cu^{2+}$ in the system.

4. The method according to claim 1, characterized in that: in step (1), a molar ratio of 4-bromo-1,8-naphthalic anhydride to n-butylamine is 1:1.3, and the intermediate A is prepared using 4-bromo-1,8-naphthalic anhydride and n-butylamine as raw materials in the presence of an organic solvent and under the protection of nitrogen; in step (2), a molar ratio of the intermediate A to hydrazine hydrate is 1:5.3, and the intermediate B is prepared using the intermediate A and hydrazine hydrate as raw materials in the presence of the organic solvent; in step (3), a molar ratio of the intermediate B to glyoxal is 1:(13.3 to 15.5), and the intermediate C is prepared using the intermediate B and glyoxal as raw materials in the presence of the organic solvent; in step (4), a molar ratio of the intermediate C to trihydroxymethyl aminomethane is 1:(1 to 1.6), and the 1,8-naphthalimide derivative is prepared using the intermediate C and trihydroxymethyl aminomethane as raw materials in the presence of the organic solvent; the reaction temperature for preparing the 1,8-naphthalimide derivative is 25° C. to 80° C., and a reaction time is 6 h to 24 h.

5. The method according to claim 2, characterized in that: in step (5), the organic solvent is acetonitrile; when the solvent is an organic solvent and water, a volume ratio of the organic solvent to water is less than or equal to 1/99; and a final concentration of 1,8-naphthalimide derivative is 10 µM.

6. The method according to claim 1, characterized in that: the 1,8-naphthalimide derivative has the following chemical structural formula:

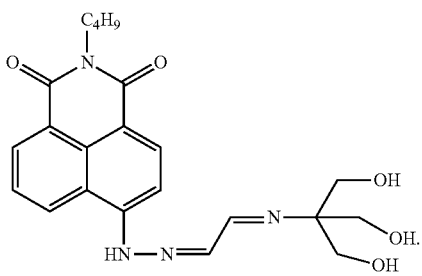

7. The method according to claim 6, further comprising:
preparing a $Cu^{2+}$ fluorescent probe, a pH colorimetric switch, pH colorimetric switch materials, a $Cu^{2+}$ fluorescent probe system, or a pH colorimetric switch system,
wherein the $Cu^{2+}$ fluorescent probe, the pH colorimetric switch, the pH colorimetric switch materials, the $Cu^{2+}$ fluorescent probe system, and the pH colorimetric switch system include the 1,8-naphthalimide derivative.

8. The method according to claim 7, characterized in that: an application environment of the $Cu^{2+}$ fluorescent probe, the pH colorimetric switch, the pH colorimetric switch materials, the $Cu^{2+}$ fluorescent probe system, and the pH colorimetric switch system is an organic solvent and/or water environment; in the application, a final concentration of the 1,8-naphthalimide derivative is 10 μM.

9. A method for pH colorimetry of a solution to be tested, comprising the following steps:
adding a 1,8-naphthalimide solution to the solution to be tested to obtain a mixed system,
then testing an ultraviolet-visible absorption spectrum of the mixed system, and
completing the pH colorimetry of the solution to be tested according to color of the mixed system, ultraviolet-visible absorption wavelength, and absorbance,
wherein the 1,8-naphthalimide solution includes the 1,8-naphthalimide derivative according to claim 6.

10. The method according to claim 9, characterized in that: a concentration of the 1,8-naphthalimide derivative in the mixed system is 10 μM; when the mixed system contains an organic solvent and water, a volume ratio of the organic solvent to water is less than 4.

11. The method according to claim 2, characterized in that: in step (1), a molar ratio of 4-bromo-1,8-naphthalic anhydride to an n-butylamine is 1:1.3, and the intermediate A is prepared using 4-bromo-1,8-naphthalic anhydride and n-butylamine as raw materials in the presence of an organic solvent and under the protection of nitrogen; in step (2), a molar ratio of the intermediate A to hydrazine hydrate is 1:5.3, and the intermediate B is prepared using the intermediate A and hydrazine hydrate as raw materials in the presence of the organic solvent; in step (3), a molar ratio of the intermediate B to glyoxal is 1:(13.3 to 15.5), and the intermediate C is prepared using the intermediate B and glyoxal as raw materials in the presence of the organic solvent; in step (4), a molar ratio of the intermediate C to trihydroxymethyl aminomethane is 1:(1 to 1.6), and the 1,8-naphthalimide derivative is prepared using the intermediate C and trihydroxymethyl aminomethane as raw materials in the presence of the organic solvent; a reaction temperature for preparing the 1,8-naphthalimide derivative is 25° C. to 80° C., and a reaction time is 6 h to 24 h.

12. The method according to claim 3, characterized in that: in step (1), a molar ratio of 4-bromo-1,8-naphthalic anhydride to n-butylamine is 1:1.3, and the intermediate A is prepared using 4-bromo-1,8-naphthalic anhydride and n-butylamine as raw materials in the presence of an organic solvent and under the protection of nitrogen; in step (2), a molar ratio of the intermediate A to hydrazine hydrate is 1:5.3, and the intermediate B is prepared using the intermediate A and hydrazine hydrate as raw materials in the presence of the organic solvent; in step (3), a molar ratio of the intermediate B to glyoxal is 1:(13.3 to 15.5), and the intermediate C is prepared using the intermediate B and glyoxal as raw materials in the presence of the organic solvent; in step (4), a molar ratio of the intermediate C to trihydroxymethyl aminomethane is 1:(1 to 1.6), and the 1,8-naphthalimide derivative is prepared using the intermediate C and trihydroxymethyl aminomethane as raw materials in the presence of the organic solvent; a reaction temperature for preparing the 1,8-naphthalimide derivative is 25° C. to 80° C., and a reaction time is 6 h to 24 h.

* * * * *